US009945382B2

(12) United States Patent
Naidyhorski et al.

(10) Patent No.: US 9,945,382 B2
(45) Date of Patent: Apr. 17, 2018

(54) REDUCING CENTRIFUGAL PUMP BEARING WEAR THROUGH DYNAMIC MAGNETIC COUPLING

(71) Applicant: Medtronic, Inc., Minneapolis, MN (US)

(72) Inventors: Roger A. Naidyhorski, Plymouth, MN (US); Brian J. Steffens, Maple Grove, MN (US); Craig D. Petersen, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/337,306

(22) Filed: Oct. 28, 2016

(65) Prior Publication Data

US 2017/0045054 A1    Feb. 16, 2017

Related U.S. Application Data

(62) Division of application No. 13/544,596, filed on Jul. 9, 2012.

(51) Int. Cl.

| *F04D 13/02* | (2006.01) |
| *F04D 27/00* | (2006.01) |
| *F04D 29/04* | (2006.01) |
| *F04D 25/02* | (2006.01) |
| *F04D 15/00* | (2006.01) |

(Continued)

(52) U.S. Cl.
CPC ......... *F04D 13/027* (2013.01); *F04D 13/024* (2013.01); *F04D 13/06* (2013.01); *F04D 13/064* (2013.01); *F04D 15/0027* (2013.01); *F04D 25/026* (2013.01); *F04D 27/002* (2013.01); *F04D 29/041* (2013.01); *F04D 29/042* (2013.01); *A61M 1/101* (2013.01); *A61M 1/1012* (2014.02); *A61M 1/1013* (2014.02); *A61M 1/1015* (2014.02); *A61M 1/1036* (2014.02); *A61M 1/1086* (2013.01); *A61M 2205/3334* (2013.01); *F04D 1/00* (2013.01); *F04D 13/026* (2013.01); *F04D 29/22* (2013.01); *F04D 29/605* (2013.01)

(58) Field of Classification Search
CPC .... F04D 13/024–13/027; F04D 27/002; F04D 29/607; F04D 29/052; F04D 29/2266; F04D 29/041–29/042; F04D 15/0027; F04D 25/026
USPC ............. 417/420; 310/419; 464/29; 318/696
See application file for complete search history.

(56) References Cited

U.S. PATENT DOCUMENTS

| 2,230,717 A | 2/1941 | DeLancey |
| 2,970,548 A | 2/1961 | Vilhelm |

(Continued)

*Primary Examiner* — Alexander Comley (57) ABSTRACT

A pump drive for an extracorporeal blood pumping system including an adjustable drive magnet. The pump drive may be coupled to a blood pump which includes a pump impeller. The pump drive may include a stepper motor for dynamically adjusting the position of the drive magnet. The position of the drive magnet may be varied to vary the distance between the drive magnet and an impeller magnet of the pump impeller. Adjusting the position of the drive magnet may include dynamically adjusting the drive magnet and may include axially moving the drive magnet to thereby vary a magnetic attraction force between the drive magnet and the impeller magnet which may thereby minimize forces acting on one or more bearings of a pump impeller.

9 Claims, 5 Drawing Sheets

(51) Int. Cl.
  *F04D 13/06* (2006.01)
  *F04D 29/041* (2006.01)
  *F04D 29/042* (2006.01)
  *F04D 29/60* (2006.01)
  *A61M 1/10* (2006.01)
  *F04D 1/00* (2006.01)
  *F04D 29/22* (2006.01)

(56) References Cited

U.S. PATENT DOCUMENTS

| | | | |
|---|---|---|---|
| 3,052,805 A | 9/1962 | Hudson | |
| 3,198,125 A | 8/1965 | Yuza | |
| 3,299,819 A | 1/1967 | McCoy | |
| 3,306,221 A | 2/1967 | Wayne | |
| 3,366,903 A * | 1/1968 | Searle | F16D 63/002 188/267 |
| 3,411,450 A | 11/1968 | Clifton | |
| 3,415,195 A | 12/1968 | Catterson | |
| 3,802,804 A | 4/1974 | Zimmermann | |
| 3,957,389 A | 5/1976 | Rafferty et al. | |
| 3,970,408 A | 7/1976 | Rafferty et al. | |
| 4,037,984 A | 7/1977 | Rafferty et al. | |
| 4,065,234 A | 12/1977 | Yoshiyuki | |
| 4,115,040 A | 9/1978 | Knorr | |
| 4,152,099 A | 5/1979 | Bingler | |
| 4,239,092 A * | 12/1980 | Janson | F16D 27/01 188/267 |
| 4,589,822 A | 5/1986 | Clausen et al. | |
| 4,643,641 A * | 2/1987 | Clausen | A61L 2/206 415/170.1 |
| 4,722,661 A | 2/1988 | Mizuno | |
| 4,856,631 A * | 8/1989 | Okamoto | F16D 37/02 192/110 R |
| 4,927,337 A * | 5/1990 | Lustwerk | F04D 29/2222 310/104 |
| 4,984,972 A * | 1/1991 | Clausen | F04D 5/001 415/900 |
| 5,021,048 A | 6/1991 | Buckholtz | |
| 5,090,944 A | 2/1992 | Kyo | |
| 5,147,186 A | 9/1992 | Buckholtz | |
| 5,158,279 A * | 10/1992 | Laffey | B65H 3/5261 192/110 R |
| 5,292,284 A * | 3/1994 | Denk | H02K 49/06 310/104 |
| 5,360,317 A * | 11/1994 | Clausen | F04D 29/0413 415/206 |
| 5,368,439 A * | 11/1994 | Piazza | F04D 29/167 415/131 |
| 5,575,630 A * | 11/1996 | Nakazawa | F04D 13/026 415/900 |
| 5,640,983 A * | 6/1997 | Sherman, Jr. | B05B 3/0445 134/167 R |
| 5,803,720 A * | 9/1998 | Ohara | A61M 1/1036 415/206 |
| 5,947,703 A | 9/1999 | Nojiri et al. | |
| 5,971,023 A | 10/1999 | Clague et al. | |
| 5,993,176 A | 11/1999 | Kingsford et al. | |
| 6,007,303 A * | 12/1999 | Schmidt | H02K 49/104 123/41.47 |
| 6,015,275 A * | 1/2000 | Suzuki | F04D 29/048 310/90.5 |
| 6,071,093 A | 6/2000 | Hart | |
| 6,129,660 A | 10/2000 | Nakazeki et al. | |
| 6,142,752 A * | 11/2000 | Akamatsu | F04D 15/0066 417/44.2 |
| 6,208,053 B1 * | 3/2001 | Scott | H02K 49/065 192/84.1 |
| 6,227,817 B1 | 5/2001 | Paden | |
| 6,293,752 B1 | 9/2001 | Clague et al. | |
| 6,338,681 B1 * | 1/2002 | Lin | G01C 15/004 33/290 |
| 6,439,845 B1 * | 8/2002 | Veres | F04D 13/0666 415/206 |
| 6,589,031 B2 | 7/2003 | Maeda et al. | |
| 6,619,935 B1 | 9/2003 | Kluth et al. | |
| 6,682,430 B2 * | 1/2004 | Killen | H02K 49/046 192/84.5 |
| 6,722,863 B2 * | 4/2004 | Maeda | F04D 13/026 415/206 |
| 6,884,210 B2 * | 4/2005 | Nose | A61M 1/1017 600/16 |
| 7,322,805 B2 | 1/2008 | Biver et al. | |
| 7,528,514 B2 * | 5/2009 | Cruz | F16D 27/01 310/103 |
| 7,690,335 B2 | 4/2010 | Togawa et al. | |
| 8,029,246 B2 | 10/2011 | Hanai et al. | |
| 8,079,828 B2 | 12/2011 | Togawa et al. | |
| 8,210,829 B2 | 7/2012 | Horvath et al. | |
| 2004/0066107 A1 | 4/2004 | Gery | |
| 2005/0008496 A1 | 1/2005 | Tsubouchi et al. | |
| 2006/0222533 A1 * | 10/2006 | Reeves | F04D 13/021 417/420 |
| 2007/0243085 A1 | 10/2007 | Adachi et al. | |
| 2010/0132138 A1 * | 6/2010 | Jorgensen | B08B 9/0936 15/21.1 |
| 2011/0002794 A1 * | 1/2011 | Haefliger | F04D 29/0413 417/53 |
| 2012/0315998 A1 * | 12/2012 | Danielsson | B08B 9/0936 464/29 |

* cited by examiner

REDUCING CENTRIFUGAL PUMP BEARING WEAR THROUGH DYNAMIC MAGNETIC COUPLING

RELATED APPLICATIONS

This application is a Division of and claims the benefit of U.S. patent application Ser. No. 13/544,596, filed Jul. 9, 2012. The disclosure of which is herein incorporated by reference in its entirety.

BACKGROUND

Extracorporeal blood pumps are used to assist patient blood circulation in a variety of surgical procedures including both short and relatively longer-term procedures including cardiopulmonary bypass (CPB) Extracorporeal Membrane Oxygenation (ECMO) or Extracorporeal Life Support (ECLS). One type of blood pump commonly used is a magnetically driven centrifugal blood pump which includes an external drive motor that drives the blood pump via magnetic coupling between a drive motor magnet and a blood pump impeller magnet. Magnetic coupling in this manner allows for the centrifugal blood pump to be housed in a separate and disposable sealed unit and discarded after a single use while the pump drive may be reusable.

Magnetically driven centrifugal blood pumps may include one or more bearings. In some magnetically driven centrifugal blood pumps, a pump impeller is captured between an upper and a lower bearing and as the impeller spins or turns, the pressure distribution of the pumped fluid (e.g. blood) generates an upward or impeller lift force which acts on the upper bearing. Conversely, the magnetic attraction between the impeller magnet and the drive magnet results in a downward force which acts on the lower bearing. The net force on the bearings is the summation of these two forces. Over time, the forces acting on the bearings may result in a finite bearing life. Therefore, it would be advantageous to minimize forces acting on the bearings so as to extend bearing life. Extending the life of the blood pump bearings may advantageously allow for use of the blood pump in extended or longer term procedures or applications.

SUMMARY

Aspects of the present disclosure provide devices, systems and methods for dynamically adjusting a drive magnet of a pump drive used in an extracorporeal blood pumping system. Apparatus and methods according to the disclosure include an extracorporeal blood pumping system comprising a centrifugal blood pump with a pump impeller wherein the pump impeller comprises an impeller magnet. The system further comprising a pump drive including a drive motor coupled to a drive magnet. The blood pump and pump drive may be coupled together magnetically and may be mechanically coupled together to provide a blood pump-pump drive assembly. The drive magnet position may be adjusted such that the distance between the drive magnet and impeller magnet is varied. Adjustment of the drive magnet may comprise axial displacement of the drive magnet.

Apparatus and methods according to the disclosure also include a blood pump magnetically coupled to a pump drive where the blood pump includes an impeller magnet embedded within a pump impeller and the pump drive includes a drive motor coupled to a drive magnet. The pump impeller may be positioned within a blood pump housing between upper and lower bearings. Actuation of the pump impeller may generate a lift force which may cause the pump impeller to act on the upper bearing. A magnetic attraction force between the impeller magnet and the drive magnet may cause the pump impeller to act on the lower bearing. A stepper motor may be configured to axially displace the drive magnet such that the magnetic attraction force is approximately equal and opposite the lift force. Further, when the magnetic attraction force and lift force are approximately equal and opposite, axial forces acting on the bearings may be minimized.

Aspects according to the disclosure further provide a method of minimizing wear on at least one bearing of a centrifugal blood pump which may include varying the position of a drive magnet of a pump drive coupled to the blood pump such that a magnetic attraction force between an impeller magnet of the blood pump and the drive magnet is approximately equal and opposite a pump impeller lift force. The method may comprise varying the position of a drive magnet, varying a relative distance between a drive magnet and an impeller magnet, axially moving or adjusting a drive motor, actuating a stepper motor, and or actuating a drive motor housing and/or drive motor carrier. The method may also comprise communicating a drive motor speed to a system controller and may comprise correlating the drive motor speed to a stepper motor position.

Methods according the disclosure may include a method of adjusting a position of a drive magnet of a pump drive comprising actuating a stepper motor coupled to the drive magnet. Actuating the stepper motor may thereby cause a drive motor housing to spin or turn causing a threadably coupled drive motor carrier to move axially. Where the drive magnet is coupled to the drive motor carrier, axial movement of drive motor carrier may cause the drive magnet to move or adjust axially. Actuation of the stepper motor may comprise transmitting a drive motor speed to a system controller, determining a stepper motor position corresponding to the drive motor speed and actuating the stepper motor. Determining the stepper motor position may comprise referencing a lookup table.

Methods according to the disclosure may include a method of varying a distance between a blood pump drive magnet and a blood pump impeller magnet including transmitting a drive motor speed from a drive motor to a system controller, determining a drive magnet position based upon the drive motor speed and actuating a stepper motor to displace the drive motor axially which thereby displaces a drive magnet. Determining the drive magnet position may comprise referencing a software lookup table or tables. The software lookup table may provide a stepper motor position, corresponding to the drive motor speed transmitted to the system controller which may in turn communicate the desired stepper motor position to a stepper controller. Actuating the stepper motor may further include sending a stepper motor signal to the stepper motor via wireless telemetry or a wired connection. Upon receiving the stepper motor signal indicating stepper position, the stepper motor may turn or spin to the position communicated via the signal. According to some methods, turning the stepper motor may likewise turn the stepper motor drive shaft which accordingly turns drive motor housing. Turning drive motor housing may allow drive motor carrier to move axially allowing the drive magnet to move axially where the drive magnet is coupled to the drive motor by way of a drive motor shaft.

DETAILED DESCRIPTION

Figures 1A, 1B, 2:
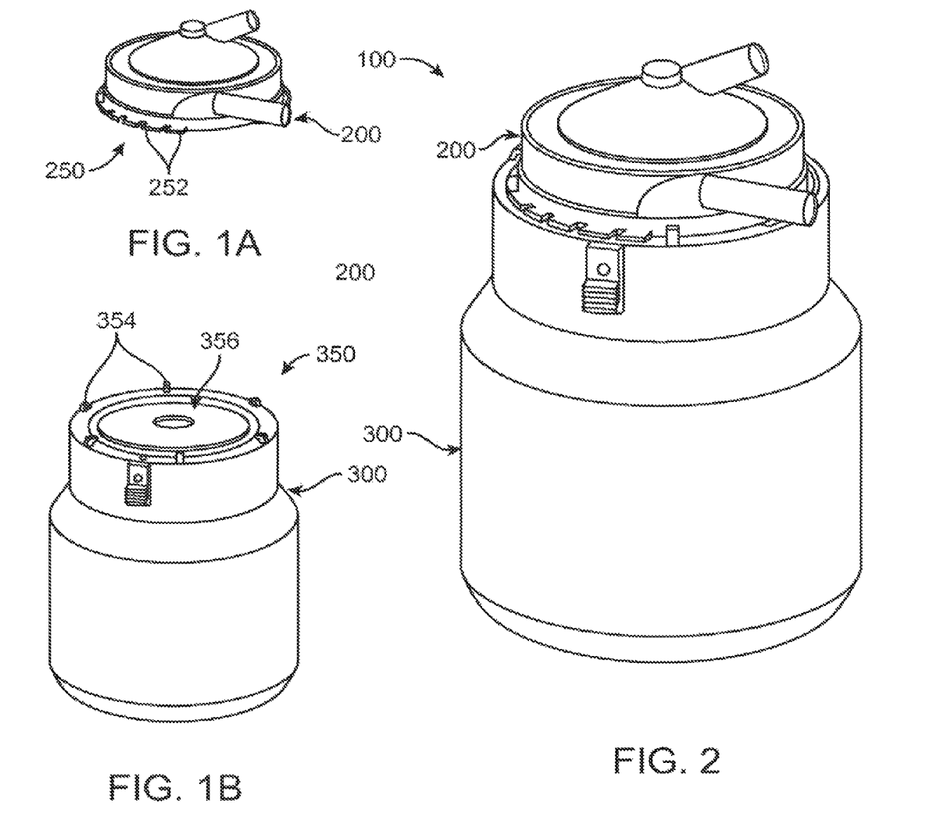
FIG. 1A depicts a blood pump useful with the disclosure.
FIG. 1B depicts a pump drive in accordance with an embodiment.
FIG. 2 depicts a blood pump-pump drive assembly in accordance with an embodiment.
Figure 4:
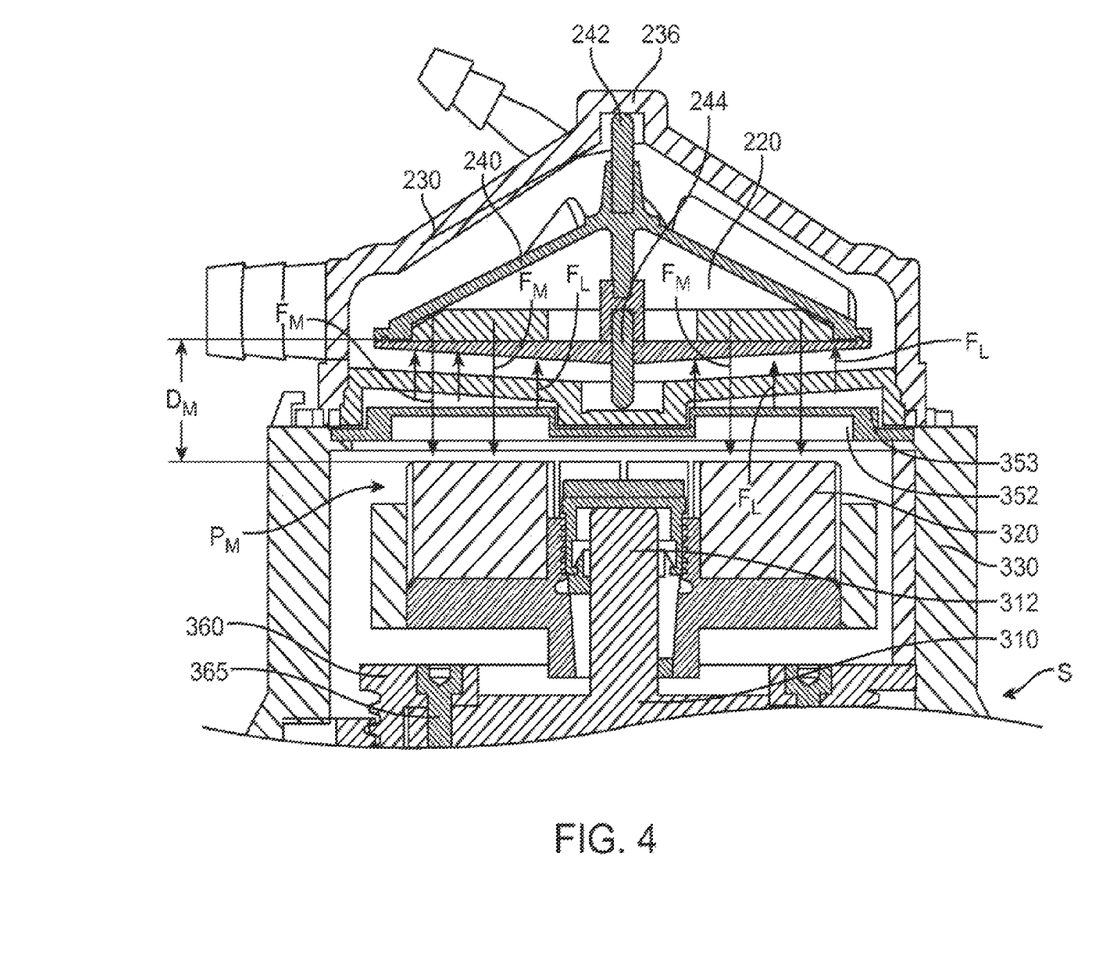
FIG. 4 depicts a partial view of the cross-section of FIG. 3.

FIGS. 1A and 2 depict a blood pump 200 of the centrifugal type used to pump blood of a patient, for example to an oxygenator (not shown) during a surgical procedure such as described herein above. Blood pump 200 includes a blood pump interface 250 including flange members 252 for coupling to an external pump drive 300 (e.g. FIGS. 1B, 2). Pump drive 300 likewise includes a pump drive interface 350 including bracket members 354 for capturing flange members 252 to couple blood pump 200 to pump drive 300 and a raised portion 356 which defines an inner recess 352 (FIG. 4). It is to be understood that pump drive interfaces 250, 350 may comprise various alternative mechanisms tor coupling pump drive 200 to blood pump 300 including fittings, brackets, notches, quick connects, clasps, and/or latches. Regardless of the specific coupling mechanism, blood pump 200 and pump drive 300 may be coupled together at the interfaces 250, 350 to define a blood pump-pump drive assembly 100 such as depicted in FIG. 2.

Figure 3:
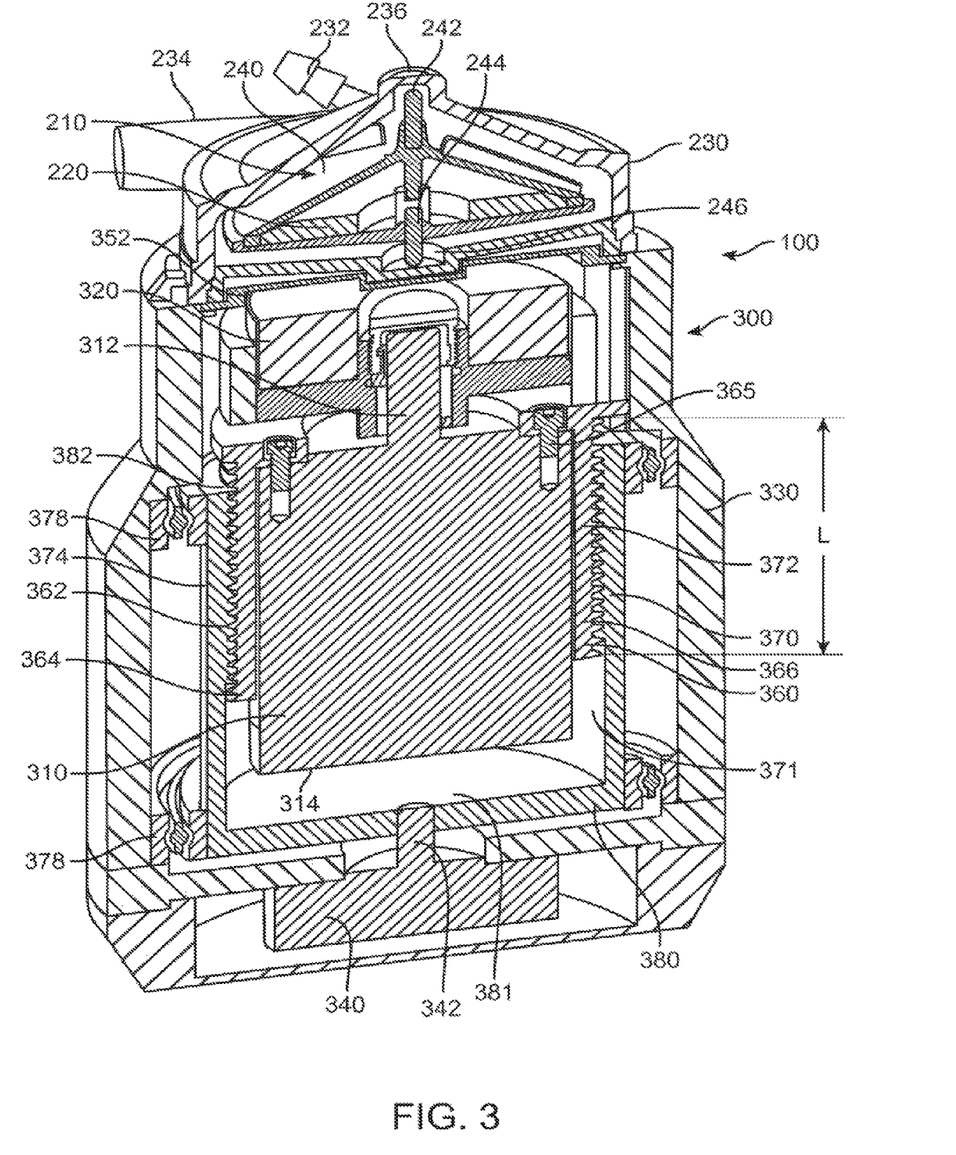
FIG. 3 depicts a cross-sectional view of the blood pump-pump drive assembly of FIG. 2.

FIG. 3 depicts the blood pump-pump drive assembly 100 of FIG. 2 in cross section. Blood pump 200 comprises a blood pump housing 230, with a blood inlet 232 and a blood outlet 234 extending from the housing 230. A pump impeller assembly 210 is contained within the pump housing 230 and comprises a pump impeller 240 configured or adapted to rotate within the housing 230 to move fluid by a centrifugal force generated by the rotation. A pump impeller magnet 220 is provided in the pump impeller assembly 210 and may be embedded in pump impeller 240 as shown. The pump impeller 240 may comprise one or more bearings and, for example, may be located or captured between an upper pivot bearing 242 and a lower pivot bearing 244. As depicted in the embodiment of FIG. 3, the upper pivot bearing 242 may abut an inner upper bearing surface 236 of blood pump housing 230 and the lower pivot bearing 244 may abut an inner lower bearing surface 246 of blood pump housing 230. Blood pump 200 may comprise any magnetically coupleable centrifugal blood pump and may for example comprise an AFFINITY™ CP centrifugal blood pump manufactured by Medtronic. Inc. of Minneapolis. Minn.

As depicted in FIG. 3, the blood pump-pump drive assembly 100 includes pump drive 300 comprising a pump drive housing 330. A blood pump drive motor 310 and a thrust force, or pump drive magnet 320, are contained within the pump drive housing 330. The drive magnet 320 may comprise one or more magnets. The drive motor 310 communicates with a control assembly (e.g. 400 FIG. 6) which is configured to actuate the drive motor 310. Actuation of the drive motor 310 actuates the drive magnet 320 via a drive shaft 312. Actuation of the drive magnet 320 causes the drive magnet 320 to spin at the speed (RPM) of the drive motor 310 and thus may comprise direct drive mechanism. Alternatively, systems comprising gearing or transmission (not shown) may be used to drive the drive magnet 320. Regardless, when the drive magnet 320 is located in sufficient proximity to the pump impeller magnet 220, such as when the blood pump 200 is coupled to the pump drive 300, (i.e. as in assembly 100), actuation of the drive magnet 320 generates a torque in the impeller magnet 220 through magnetic coupling which in turn causes pump impeller 240 to spin at the rate of speed (RPM) of the drive magnet 320. Containment of the blood pump 200 in a housing 230 separate from both the drive motor 310 and the pump drive housing 330, enables the blood pump 200 to be discarded after a single use (e.g. after having been contaminated with patient blood during a surgical procedure) while the pump drive 300 may be reusable.

With continued reference to FIG. 3 pump drive 300 includes a drive motor carrier 360 attached to drive motor 310. Drive motor earner 300 is configured to travel or adjust axially upon rotation of a drive motor housing 370 as explained in further detail below. Attachment of the drive motor 310 to the drive motor carrier 360 may be accomplished via socket head cap screws 365 as shown or via any fastening or attaching device or means including, but not limited to adhesives, clips, screws, bolts, pins, rivets, and/or rods. Drive motor canter 360 may comprise a cylinder shape with an open distal or bottom end 364 through which drive motor 310 is allowed to extend, as illustrated in FIG. 3. The drive motor earner 360 further comprises a wall 366 which may extend to any length L along the drive motor 310. For example, wall 366 may extend to any length which allows for sufficient travel of the drive motor 310 and drive magnet 320 such as described in further detail with reference to FIG. 5. As further examples, the wall 366 may extend to any length above a bottom or distal end 314 of drive motor 310 such as illustrated, to the end 314 or past the end 314. In any case, drive motor carrier 360 includes an outer surface threaded interface 362 for coupling with an inner surface threaded interface 372 of drive motor housing 370. Drive motor carrier 360 may partially, substantially or completely surround a portion of the drive motor 310 and may partially or substantially conform to the shape of the drive motor 310 or may comprise other configurations provided that the drive motor 310 is coupled to the drive motor currier 360.

Drive motor housing 370 defines a chamber 371 for receiving the drive motor 310 attached to drive motor carrier 360 and includes an open proximal end 382 configured to allow travel of the drive motor carrier 360, and thus drive motor 310, therethrough. When the drive motor 310 coupled to drive motor carrier 360 is received within chamber 371, the drive motor housing 370 surrounds at least a portion of the drive motor carrier 360 and is coupled to the drive motor carrier 360 via engagement of inner surface threaded interface 372 of housing 370 with outer surface threaded interface 362 of the drive motor carrier 360. An outer surface 374 of drive motor housing 370 may abut one or bearings 378 which may comprise any type of bearing, for example the ball bearing as depicted in FIG. 3. As shown in the example of FIG. 3, an outer surface 374 of drive motor housing 370 abuts two bearings 378, one at each of a distal end 380 and a proximal end 382 of housing 370.

In operation, the drive motor housing 370 is configured to turn or spin upon actuation of a stepper motor 340. Stepper motor 340 may be coupled to drive motor housing 370 via a shaft 342. The turning or spinning of drive motor housing 370 causes drive motor carrier 360 to travel axially due to coupling of the drive motor carrier 360 to the drive motor housing 370 at threaded interfaces 362, 372.

Figure 5A:
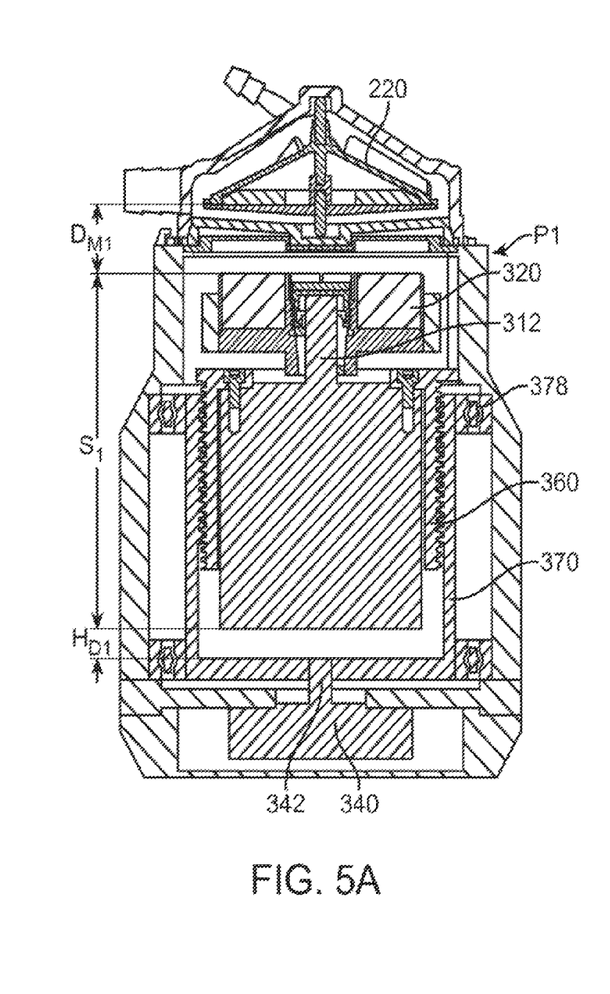
FIG. 5A depicts the blood pump-pump drive assembly of FIG. 3 with a drive magnet in a position in accordance with an embodiment.
Figure 5B:
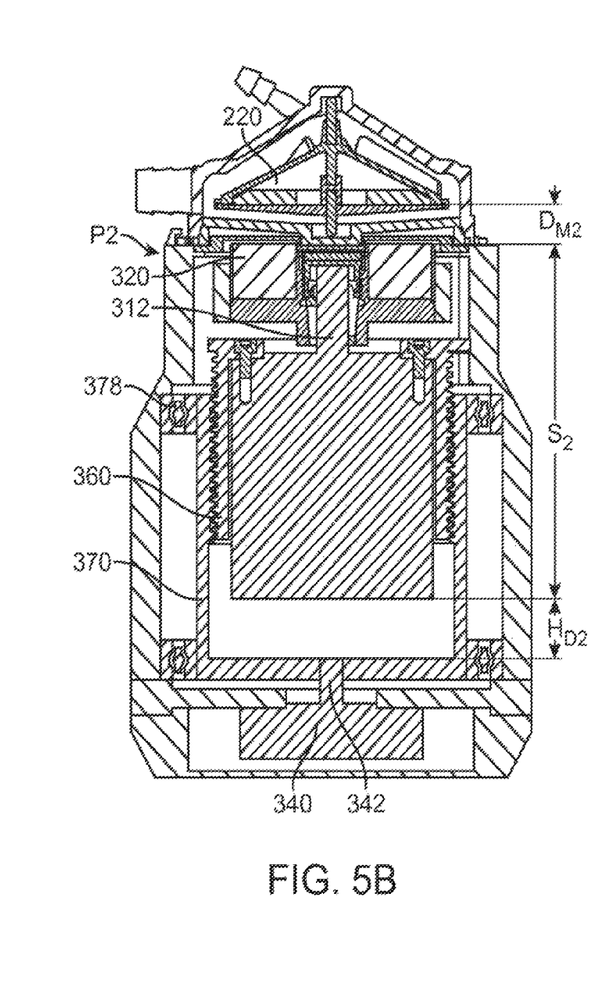
FIG. 5B depicts the blood pump-pump drive assembly of FIG. 3 with a drive magnet in a position in accordance with an embodiment.

With reference between FIG. 3 and FIGS. 5A-5B, FIG. 5A depicts drive motor carrier 360 with drive motor 310 at a first drive motor height $H_{D1}$ where $H_{D1}$ is measured from a distal end inner surface 381 of drive motor housing 370 to a distal end 314 (FIG. 3) of drive motor 310. Actuation of stepper motor 340, described in further detail with reference to FIG. 6, below, causes stepper motor drive shaft 342 to rotate thereby turning drive motor housing 370 either clockwise or counterclockwise, depending upon the desired axial positioning of drive magnet 320. When drive motor housing 370 turns at the threaded interface defined by inner surface threaded interface 372 and outer surface threaded interface 362, drive motor carrier 360 may travel axially relative to the distal end 380 of drive motor housing 370. Drive motor carrier 360 is configured to travel axially either in a proximal direction or a distal direction (i.e. up or down relative to a bottom or distal end 380 of drive motor housing 370) depending upon clockwise or counterclockwise rotation of drive motor housing 370. Since drive motor carrier 360 is coupled to drive motor 310 and drive magnet 320 is coupled to drive motor 310, axial movement of drive motor carrier 360 axially displaces drive magnet 320. For example, drive magnet 320 may comprise a First drive magnet position (e.g. $P_1$, FIG. 5A), or a second drive magnet position (e.g. P2, FIG. 5B). Drive magnet 320 in a First drive magnet position $P_1$ may correspond to the drive motor 310 at a first drive motor height $H_{D1}$ and may correspond to a distance $D_{M1}$ between drive magnet 320 and impeller magnet 320. Likewise, drive magnet position $P_2$ may correspond to the drive motor 310 at a second drive motor height $H_{D2}$ and a distance $D_{M2}$ between drive magnet 320 and impeller magnet 220. Thus, when drive magnet 320 travels proximally or in an upward direction relative to a distal end 380 of drive motor housing 370, the drive magnet 320 moves into closer proximity to the impeller magnet 220 of the coupled centrifugal blood pump 200 and a distance $D_M$ (FIG. 4) between the impeller magnet 220 and the drive magnet 320 decreases. By the same token, when drive magnet 320 travels or moves distally or in a downward direction (i.e. toward distal end 380 of drive motor housing 370), the drive magnet 320 moves away from the impeller magnet 220 of the coupled blood pump 200 such that the distance $D_M$ increases. A recess portion. 352 (FIGS. 3-5) of pump drive 300 is configured to allow drive magnet 220 to be received therein such as upon upward or proximal axial displacement, of the drive magnet 320 toward the impeller magnet 220.

FIGS. 5A and 5B depict two different positions, P1 and P2 of drive magnet 320. Nevertheless, drive magnet 320 may be positioned at various incremental axial positions, not specifically illustrated. Axial displacement or travel of the drive magnet 320 may be limited or bound at a proximal or upper end by recess portion 352 of drive motor housing 330 such that when a portion of drive magnet 320 is adjacent (e.g. contacts or substantially contacts) an inner surface 353 of recess portion 352, no further upward or proximal travel is allowed. Conversely, distal or downward travel of drive magnet 320 may be limited or bound by drive motor housing distal end 380 such that when a portion of drive motor 310 (or a portion of drive motor carrier 360, if drive motor carrier 360 extends beyond drive motor distal end 314) reaches or is adjacent (e.g. contacts or substantially contacts) drive motor housing distal end 380, no further distal or downward travel of the drive motor earner 360 or drive motor 310 may be permitted.

With the above description in mind, FIG. 4 depicts forces which may act on pump impeller 240. A net impeller lift force $F_L$, illustrated by upward or proximally directed arrows may be generated as the pump impeller 240 spins. Impeller lift force $F_L$ is a net pressure distribution force and may vary with pump impeller speed, and fluid (e.g. blood) properties. Rotation (RPM) of the pump impeller 240 may cause a pressure differential which generates a Bernouli effect in a rotational motion thereby causing the pump impeller 240 to lift. Also depicted in FIG. 4 is a net magnetic attraction force, $F_M$, illustrated by downward or distally directed arrows which may be generated between the drive magnet 320 and the impeller magnet 220 when the drive magnet 320 and impeller magnet 220 are in sufficient proximity or located a sufficient distance $D_M$ apart. Adjusting the position $P_M$ of the drive magnet 320 relative to the impeller magnet 220 may vary the magnetic attraction force $F_M$. As described above, impeller lift force Ft may act on pump impeller 240 such that upper pivot bearing 242 bears against upper bearing surface 236 and may thereby cause upper pivot bearing 242 to undergo wear. Likewise, the magnetic attraction force $F_M$ may act on the pump impeller 240 such that lower pivot bearing 244 bears against lower bearing surface 246 and may Thereby cause lower pivot bearing 246 to undergo wear.

In general, the pivot bearings 242, 244 are unidirectional such that if one is loaded, the other is not. Imbalance in forces between the two pivot bearings 244, 246 may generate heat and/or mechanical wear on the pivot bearing experiencing the higher force (e.g. $F_M$ or $F_L$). Often, as the pump impeller 240 spins, the lift force $F_L$ generated exceeds the magnetic attraction force $F_M$ such that upper pivot bearing 244 experiences more wear. This may be especially true at higher pump or impeller speeds as will be further elucidated in the ensuing discussion. Regardless, a total net force acting on the pivot bearings 244, 246 is the summation of $F_M$ and $F_L$. Therefore, varying the magnetic attraction force $F_M$ by varying the proximity of the drive magnet 320 to the impeller magnet 220 (i.e. varying drive magnet position $P_M$), such that the magnetic attraction force $F_M$ is approximately equal and opposite the lift force $F_L$, may minimize axial forces acting on each of the upper and lower pivot hearings 244, 246. As described above, varying the relative distance $D_M$ between the drive magnet 320 and impeller magnet 220 may comprise in part actuation of a stepper motor 340. Control of the stepper motor 340 is described below with reference to FIG. 6.

Figure 6:
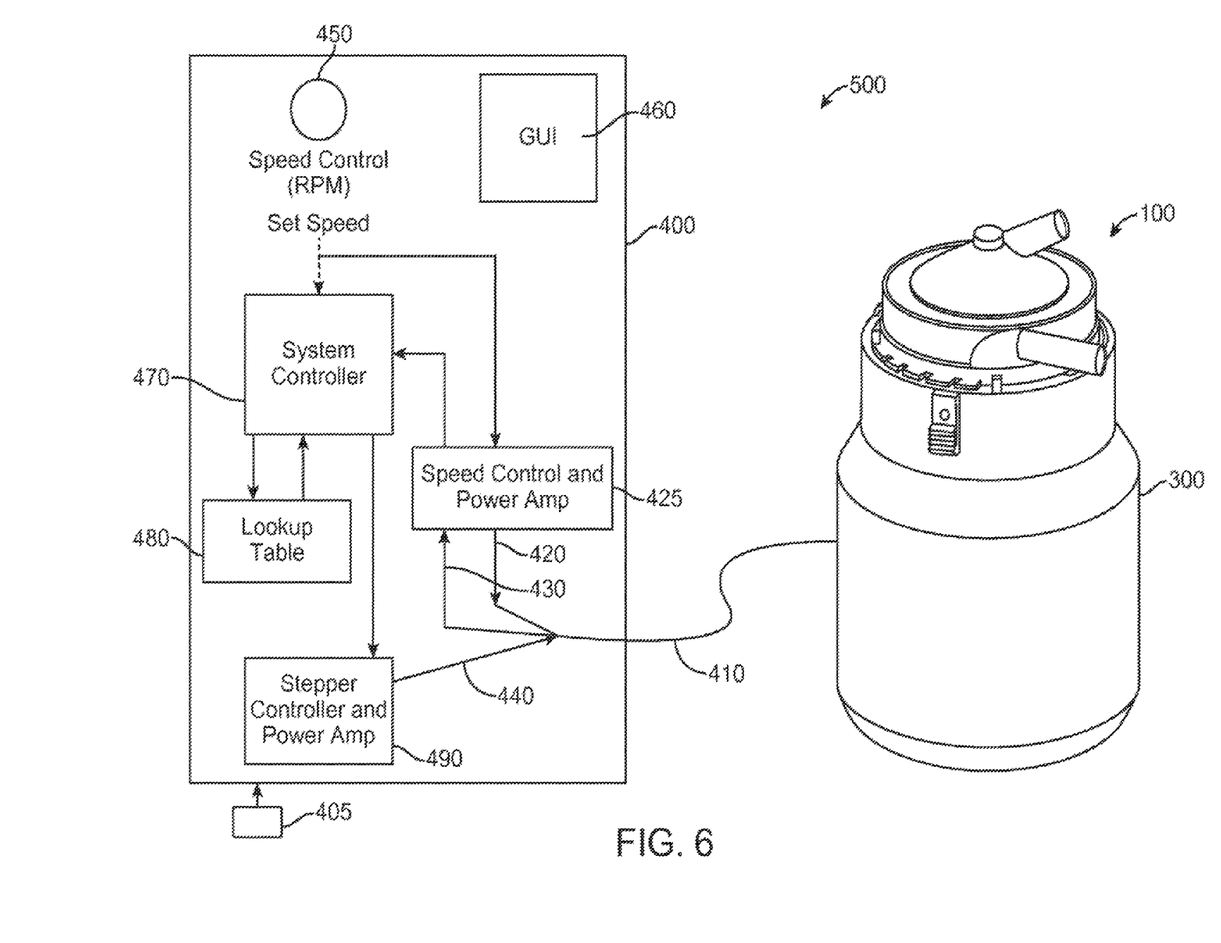
FIG. 6 depicts a diagrammatic view of a system in accordance with an embodiment.

FIG. 6 illustrates an embodiment of a system 500 including a control assembly 400 for controlling a pump drive 300 coupled to blood pump 200. The control assembly 400 may include an external power source 405, a speed control 450, and a graphic user interface 460. Pump drive 300 may communicate with the control assembly 400 via a control signal 410. Control signal 410 may comprise telemetry or may comprise electrical wiring. In addition, control assembly 400 may be provided within pump drive housing 330 or may be external to pump drive housing 330 such as depicted in FIG. 6. Regardless, control signal 410 may comprise several signals for communicating between the drive motor 310, stepper motor 340 and the control assembly 400. Control signal 410 may comprise a drive motor power/speed signal 420, a drive motor speed feedback signal 430 and/or a stepper motor signal 440. Signals 420 and 430 may communicate between a speed control and power amplifier 425, a system controller 470 CONFIRM and the drive motor 310. Signal 440 may communicate between a stepper motor controller and power amplifier 490 and the stepper motor 340.

With reference between FIGS. 5A, 5B and 6, in operation, generally system controller 470 is configured to reference a lookup table or tables 480 comprising one or more drive motor speed values each speed value corresponding to one of a plurality of stepper motor position values. The software lookup table or tables 480 may be generated by way of characterization studies evaluating lift force $F_L$ and magnetic force $F_M$ as a function of drive motor speed S (FIG. 4). Thus, the stepper motor position values may relate to a drive motor height (e.g. $H_{D1}$, $H_{D2}$) and/or drive magnet position ($P_M$) which would tend to balance forces $F_L$ and $F_M$ at each drive motor speed S during the course of a procedure or during use. In this manner, system 500 is configured to dynamically adjust the drive magnet 320 such that the proximity of the drive magnet 320 and the impeller magnet 220 is varied such that the magnetic force $F_M$ is approximately equal and opposite the impeller lift force $F_L$ during a use of the system, for example during a surgical procedure. More specifically, pre-programmed or pre-set software lookup tables 480 may comprise any of several incremental drive motor speed values (e.g. $S_1$, $S_2$, FIG. 5A-B) corresponding to a pre-determined (e.g. by way of a characterization study as explained above) stepper motor position, where each stepper motor position corresponds to a predetermined a drive magnet position $P_M$, drive motor height $H_D$, or distance $D_M$, which in turn depends upon the desired proximity of the drive magnet 320 to the impeller magnet 220. In other words, lookup tables 480 may be configured to correlate any incremental drive motor speed S to a particular stepper motor position to thereby provide a particular drive magnet position $P_M$. As described above, a desired distance $D_M$ of the drive magnet 320 and impeller magnet 220 may be that distance between drive magnet 320 and impeller magnet 220 which results in forces $F_M$ and $F_L$ being approximately balanced or equal.

By way of further illustration and as an example, FIG. 5A depicts a drive motor 310 at a point in time during operation of pump drive 300 in which the drive motor speed $S_1$ is lower (e.g. with respect to the drive motor speed $S_2$ of drive motor 310 depicted in FIG. 5B). In general, lower drive motor speeds may generate lower lift forces $F_L$ and therefore an increased tendency in tower pivot bearing 244 to experience bearing wear since the magnetic force $F_M$ may be allowed to overcome the lower lift force $F_L$ tending to cause lower pivot bearing 244 to bear against bearing surface 246. Thus, to balance forces $F_M$ and $F_L$, drive magnet 320 may be positioned at a greater distance (e.g. $D_{M1}$, FIG. 5A) from impeller magnet 220 (as compared to $D_{M2}$ of FIG. 5B) such dial the magnetic force $F_M$ is decreased thereby allowing lift force $F_L$ to have a tendency to pull or draw lower pivot bearing 244 upward and away from lower bearing surface 246 (i.e. approximately balancing the lift force $F_L$ and the magnetic force $F_M$). Conversely, higher drive motor speeds in general may generate higher lift forces $F_L$ and therefore an increased tendency in upper pivot bearing 242 to experience bearing wear since, in this case, lift force $F_L$ may exceed magnetic force $F_M$ whereby upper pivot bearing 242 may have a tendency to bear against bearing surface 246. In order to counterbalance a higher lift force $F_L$, drive magnet 320 may be positioned in closer proximity to, or, at a lesser distance from impeller magnet 220 as compared to distance $D_{M1}$ of FIG. 5A, for example drive magnet 320 may be positioned at a distance $D_{M2}$, as depicted in FIG. 5B. As discussed herein above, when drive magnet 320 is brought into closer proximity to impeller magnet 220, the magnetic force $F_M$ increases, thereby counteracting the increased or higher lift force $F_L$ whereby upper pivot bearing 242 may be drawn downward and away from upper bearing surface 236. In this manner, bearing wear on each of the upper pivot bearing 242 and lower pivot bearing 244 may be minimized.

Although the present disclosure has been described with reference to preferred embodiments, workers skilled in the art will recognize that changes can be made in form and detail without departing from the spirit and scope of the present disclosure.

What is claimed is:

1. A method of minimizing wear on at least one of an upper bearing and a lower bearing of a centrifugal blood pump comprising a pump impeller, the method comprising:
   varying a position of a pump drive magnet such that a magnetic attraction force between a pump impeller magnet and the drive magnet is approximately equal and opposite a pump impeller lift force, the impeller lift force caused by an actuation of the pump impeller;
   wherein varying the position of the pump drive magnet includes displacing a drive motor coupled to the drive magnet; and wherein displacing the drive motor comprises actuating a stepper motor coupled to the drive motor;
   wherein the stepper motor and the drive motor share a common rotation central axis;
   wherein the magnetic attraction force causes the pump impeller to act on the lower bearing and the lift force causes the pump impeller to act on the upper bearing; and
   wherein when the magnetic attraction force and the lift force are approximately equal and opposite, an axial force on each of the upper bearing and the lower bearing is minimized.

2. The method of claim 1, wherein actuating the stepper motor comprises controlling the stepper motor via a system controller.

3. The method of claim 2, wherein controlling the stepper motor via the system controller comprises:
   transmitting a drive motor speed to the system controller;
   determining a stepper motor position based upon the drive motor speed; and
   actuating the stepper motor to displace the drive motor whereby the drive magnet is axially moved.

4. The method of claim 3 wherein actuating the stepper motor comprises actuating the stepper motor via telemetry.

5. The method of claim 1, further comprising a pump drive housing defining a chamber within which the drive motor is received, wherein the stepper motor is threadably coupled to the drive motor and is configured to axially displace the drive motor; wherein the stepper motor axially displaces the drive motor relative to the pump drive housing.

6. A method of minimizing wear on at least one of an upper bearing and a lower bearing of a centrifugal blood pump comprising a pump impeller, the method comprising:
   varying a position of a pump drive magnet such that a magnetic attraction force between a pump impeller magnet and the drive magnet is approximately equal and opposite a pump impeller lift force, the impeller lift force caused by an actuation of the pump impeller; further comprising a pump drive housing defining a chamber within which a drive motor is received, wherein a stepper motor is threadably coupled to the drive motor and is configured to axially displace the drive motor; wherein the stepper motor axially displaces the drive motor relative to the pump drive housing; wherein varying the position of the pump drive magnet includes displacing the drive motor coupled to the drive magnet; and wherein displacing the drive motor comprises actuating the stepper motor coupled to the drive motor; wherein the stepper motor and the drive motor share a common rotation central axis; wherein the magnetic attraction force causes the pump impeller to act on the lower bearing and the lift force causes the pump impeller to act on the upper bearing; and wherein when the magnetic attraction force and the lift force are approximately equal and opposite, an axial force on each of the upper bearing and the lower bearing is minimized.

7. The method of claim 6, wherein actuating the stepper motor comprises controlling the stepper motor via a system controller.

8. The method of claim 7, wherein controlling the stepper motor via the system controller comprises:
   transmitting a drive motor speed to the system controller;
   determining a stepper motor position based upon the drive motor speed; and
   actuating the stepper motor to displace the drive motor whereby the drive magnet is axially moved.

9. The method of claim 8, wherein actuating the stepper motor comprises actuating the stepper motor via telemetry.

* * * * *